United States Patent [19]

Brownscombe et al.

[11] Patent Number: 5,646,193

[45] Date of Patent: Jul. 8, 1997

[54] PROCESS TO PREPARE TWO PHASE FOAM COMPOSITIONS AND TWO PHASE FOAM COMPOSITIONS

[75] Inventors: Thomas Fairchild Brownscombe; Ronald Marshall Bass; Pui Kwan Wong; George Constantine Blytas; William Peter Gergen; Maryanne Mores, all of Houston, Tex.

[73] Assignee: Shell Oil Company, Houston, Tex.

[21] Appl. No.: 560,140

[22] Filed: Nov. 17, 1995

[51] Int. Cl.$^6$ ..................................................... C08J 9/28
[52] U.S. Cl. .................................................. 521/63; 521/64
[58] Field of Search ............................................ 521/63, 64

[56] References Cited

U.S. PATENT DOCUMENTS

| | | | |
|---|---|---|---|
| 4,522,953 | 6/1985 | Barby et al. | 521/64 |
| 5,037,859 | 8/1991 | Williams, Jr. et al. | 521/55 |
| 5,061,767 | 10/1991 | Ruckenstein et al. | 526/219 |
| 5,149,720 | 9/1992 | DesMarais et al. | 521/63 |
| 5,189,070 | 2/1993 | Brownscombe et al. | 521/64 |
| 5,210,104 | 5/1993 | Bass et al. | 521/64 |

*Primary Examiner*—Morton Foelak
*Attorney, Agent, or Firm*—Del S. Christensen

[57] ABSTRACT

A process is provided for the production of a porous crosslinked polymeric foam comprising the steps of: (a) providing a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) at least 70 weight percent, based on the emulsion, of water as the internal phase (iii) an effective amount to produce the water-in-oil emulsion of a first surfactant, and (iv) a first polymerization initiator; (b) providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) at least 70 weight percent, based on the emulsion, of water as the internal phase (iii) an effective amount to produce the water-in-oil emulsion of a second surfactant, and (iv) a second polymerization initiator; (c) combining the first and second emulsions; and (d) curing said polymerizable monomers under conditions effective to polymerize and crosslink the polymer prior to significant diffusion between the emulsions. Polymeric foams can be prepared by this process that exhibit positive attributes of foams formed by curing of each of the emulsions individually.

11 Claims, 1 Drawing Sheet

PROCESS TO PREPARE TWO PHASE FOAM COMPOSITIONS AND TWO PHASE FOAM COMPOSITIONS

FIELD OF THE INVENTION

This invention relates to a process to prepare two phase foam compositions and to such two phase foam compositions.

BACKGROUND OF THE INVENTION

Polymeric foams can be generally classified as either closed-cell foams or as open-cell foams. Open-cell foams can be used as a matrix to contain various liquids and gases. They are suitable for various applications such as, for example, use in wipes and diapers, as carriers and ion exchange resins. For some of these applications, it is desirable to have porous crosslinked polymer blocks which have a very low density and a high capacity of absorbing and retaining liquids. Such high absorption capacity, low density, porous polymer blocks can be prepared by polymerizing a specific type of water-in-oil emulsion known as high internal phase emulsion having relatively small amounts of a continuous oil phase and relatively greater amounts of an internal water phase.

Such high absorption capacity, low density, foams are prepared by a process disclosed in U.S. Pat. No. 4,522,953 by polymerizing and crosslinking monomers in the continuous oil phase of a high internal phase water-in-oil emulsion with a polymerization initiator such as potassium persulfate. Generally, these high internal phase water-in-oil emulsions contain at least 90 weight percent of a water phase as the internal phase. The high ratio water-in-oil emulsions are formed by combining the oil phase with water under moderate shear. In order to obtain this high internal phase water-in-oil emulsion, a surfactant must be used to stabilize the emulsion. It is also advantageous to incorporate an electrolyte into the aqueous phase. The amount and type of electrolyte, along with the amount and type of surfactant, effects the pore size, and wicking ability of the cured foam.

Certain properties of foams can be improved by selection of monomers. For example, strength of the cured foam can be significantly improved by incorporating styrene as a monomer, and softness is generally undesirably impacted by increased levels of styrene monomer. Monomers such as 2-ethylhexyl acrylate provide good absorbency, but result in a weak foam. The total amount of liquid that a foam can hold under load is a function of both absorbency, and the strength of the foam, because weight of adsorbed liquid will cause a weak foam to collapse, thus squeezing out adsorbed liquid. Foams made from high internal phase emulsions have therefore typically incorporated a mixture of monomers to obtain a compromise of properties.

Pore size and density of the foams are also dictated by compromises between properties of the foam product.

It is also desirable for some applications of high internal phase emulsion foams to have both hydrophilic and hydrophobic regions within the same foam. Such properties would be useful, for example, as a medium for removing hydrocarbons from a stream of water. U.S. Pat. No. 5,061,767, issued on Oct. 29, 1991, discloses a polymer composite useful as permselective membranes by polymerizing an emulsion of hydrophobic and hydrophilic monomers. Preparation of a foam of having both hydrophobic and hydrophilic regions is not suggested.

Composites of foams are disclosed in U.S. Pat. No. 5,037,859. These foams are rigid foams and are prepared by first curing an emulsion to form a rigid open cell foam, such as a polystyrene foam, having a relatively large pore size, and then forcing a second emulsion into the cured polystyrene to form a smaller pore diameter foam within the polystyrene. The resultant composite foams have greater strengths and densities then foams from the first emulsion, and retain the better wicking properties of the first foam. Polymerizing an emulsion within another foam matrix inherently increases density of the resultant foam composite and therefore decreases absorbency. It would be preferred to provide a composite foam wherein properties such as absorbency are not significantly compromised in order to achieve improvements in strength and other properties.

It is therefore an object of the present invention to provide a method to prepare foams from mixtures of high internal phase emulsions wherein the resultant foams exhibit characteristics of each of two separate foam compositions, or a more desirable combination of the properties compared to a high internal emulsion foam of the components of the combined two emulsions.

SUMMARY OF THE INVENTION

According to the invention, a process for the production of a porous crosslinked polymeric material is provided, comprising the steps of:

(a) providing a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) at least 70 weight percent, based on the emulsion, of water as the internal phase (iii) an effective amount to produce the water-in-oil emulsion of a first surfactant, and (iv) a first polymerization initiator;

(b) providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) at least 70 weight percent, based on the emulsion, of water as the internal phase (iii) an effective amount to produce the water-in-oil emulsion of a second surfactant, and (iv) a second polymerization initiator;

(c) combining the first and second emulsions; and (d) curing said polymerizable monomers under conditions effective to polymerize and crosslink the polymer prior to significant diffusion between the emulsions.

Polymeric foams prepared by this process can exhibit positive attributes of foams formed by curing of each of the emulsions. For example, a foam cured from a mixture of an emulsion that would form a stronger foam, and an emulsion that would form a more absorbent foam has a significantly greater strength that a foam cured from a homogenous mixture of the same monomers, and does not compromise absorbency compared to a foam cured from a homogenous mixture of the same monomers.

DETAILED DESCRIPTION OF THE INVENTION

Figure 1:
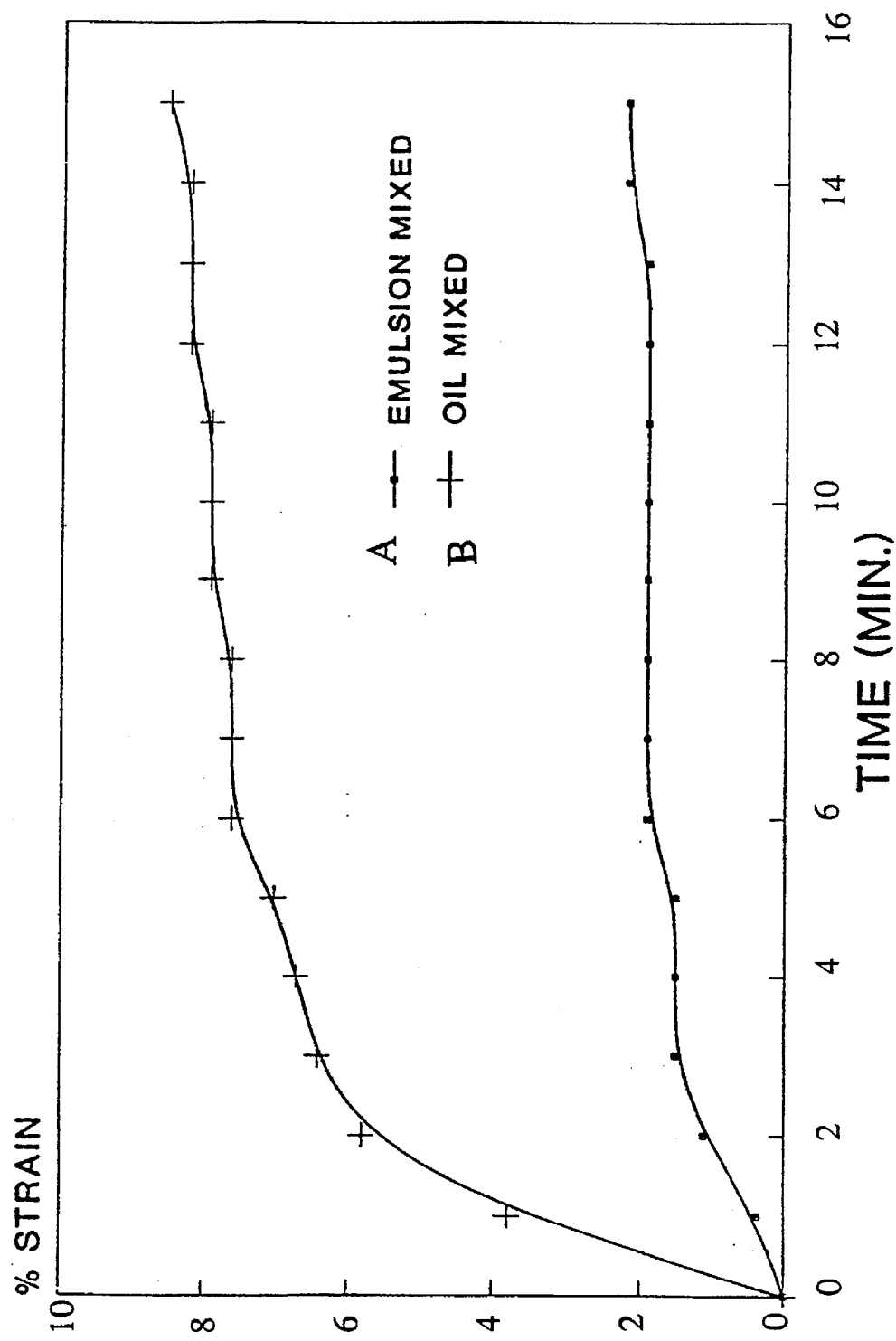
FIG. 1 is a plot of strain vs. time for an example and a comparative example of the present invention.

Phase separated foams may include foams having phases separated on a "macroscopic", a "microscopic" level, or both.

In a macroscopically phase separated foam, the phases are separated on a scale that is visible to the naked eye, or perceptible to normal probing, as with the fingers or a needle. For example, in a baby diaper, injections of an emulsion that cures to a stiff foam may be made in the material that would be under the wearer's buttocks, to support the wearer's weight, and emulsions that cure to a softer more absorbent foam may be used elsewhere. In other applications, such as covers for paint rollers, foams may be mixed in a way to provide texturing, such as for example to produce a "faux marble" appearances. This texturing may be created by differences in absorbency or wettability of the foam material. Similar principles may be applied to other applications. The foams in which phases are separated on a macroscopic level may contain phases of foams, for example, from different monomers, different surfactants, different water to oil ratios, or having been prepared using conditions that differed sufficiently to produce foams of different properties (such as pore size).

Microscopically separated phases are multiple phase foams that have phases mixed so that separate phases are not visible to the naked eye, and not perceptible to normal probing, as with fingers or a needle, but wherein "struts" of the foam lattice are of distinctly different compositions or properties. For example, in a baby diaper a phase having an attribute of being fast wicking could be microscopically combined with a more tightly absorbing fine pore sized phase of foam. Alternatively, a stronger foam may be used in combination with a foam having greater absorbency in order to have the benefit of greater strength without sacrificing significantly in absorbency. Combining monomers and providing a single emulsion often does not result in a foam having properties characteristic of each of the monomers.

One or more foam phases within a macroscopically separated foam may itself be a microscopically separated foam composition. For example, in a paint roller, it may be desirable to have one macroscopic texture area of the roller wettable by both oil and water based paints to achieve a "stipple" effect. The macroscopically separated foam of that area might contain a microscopically separated oil and water wet paint absorbing foam. In a baby diaper, soft absorbent material might be composed of a microscopic mixture of fast wicking large pore size foam, and a more tightly absorbing fine pore size foam. The support areas might be composed of different amounts of microscopically mixed stiff and resilient foams to afford comfort, and avoid the wearer's weight squeezing fluid from the foam when the baby sits up on the support areas.

In a diaper, another advantageous configuration of the present invention is to form an absorbent foam having columns of stiffer foam in potentially weight supporting regions. Such columns may be pencil lead sized columns formed by insertion of probes into a uncured or partially cured foam and injection from the probes an emulsion that includes a greater amount of a monomer such as styrene than the first emulsion. Alternatively, columns of cured or partially cured foams could be placed in a sheet of uncured or partially cured foams, the columns being sufficiently cured so that they stay together as the sheet cures around the columns. These columns may be strategically placed only where weight is to be supported, or in varying numbers or densities depending on the amount of weight to be supported.

When emulsions are combined wherein the emulsions would form foams having two different strengths, it is preferable that one of the emulsions would form a foam having a strain of greater than twenty percent (measured after five minutes under a 0.74 psi load), and another emulsion would form a foam having a strain of less than twenty percent (also measured after five minutes under a 0.74 psi load).

When two such emulsions are combined wherein the emulsions would cure to foams having different pore sizes, it is preferably that one emulsion would cure to a foam having at least 50 micron average pore size, and another emulsion would cure to a foam having less than a 50 micron average pore size.

Another application of the present invention is to provide a dispersed phase of hydrophobic foam within a matrix of a hydrophilic foam. This foam could be useful as a hydrocarbon adsorbing foam filter. The phases could be either microscopically or macroscopically mixed. Foam phases can be made to be hydrophilic by inclusion in the emulsion from which the foam is cured of polar group containing monomers, but generally, monomers sufficiently polar to result in a hydrophilic polymer will be water soluble, and partition to the water phase in the emulsion. Foams prepared from high internal phase emulsions are therefore made to be water-wetting by use of a surfactant that results in a hydrophilic head remaining at the surface of the cured polymer phase.

A foam useful to remove small amounts of water from oil may be similarly provided by using the hydrophobic phase as the continuous phase. Such a foam could be useful, for example, in a motor oil filter on an internal combustion engine.

Foam having phases of different properties may be prepared by, for example, layering different high internal phase emulsions containing continuous oil phases of polymerizable monomers prior to curing. Such layering may be used, for example, to provide a foam for use in a diaper wherein the foam next to the wearer's body is a foam having a larger pore size (therefore being a better wicking foam) and a layer away from the wearer's body that has a combination of greater strength and/or higher absorbency capacity.

Vortex mixers or other mixing devices can be used to provide either macroscopically or microscopically mixed foams. A minimal amount of experimentation with a particular mixing apparatus would be required to determine a mixing severity that results in a desired level of mixing.

Existence of two phases can be determined by visual inspection, by one of various analytical techniques, or inferred from properties of the two phase foam compositions. For example, a foam cured from a mixture of two emulsions having different monomers may exhibit two distinct glass transitions temperatures, implying that two separate phases exist. Existence of two foam phases according to the present invention can also be inferred by comparing properties of a foam cured from two emulsions to a foam cured from a single emulsion of the combination of components of the two emulsions (i.e. combining oil phase and aqueous phase components prior to preparing an emulsion). Thus, the present invention is a method to prepare such materials by combining polymerizable high internal phase emulsions in such a way that the resultant foams exhibit beneficial properties of the foams formed from each of the emulsions.

The amount of the first emulsion relative to the second emulsion can vary greatly. For example, in a macroscopically separated foam, a single identifiable separated phase may add a useful property to the foam composition. Generally, the ratio of the first to the second emulsion will be between about 5:95 to about 95:5 for either a macroscopically or a microscopically separated foam. More preferably, the ratio of the first to the second foam is between about 20:80 and about 80:20.

Analytical techniques that may be useful in determining the existence of two separate phases and the size of different domains of each phase include, but are not limited to: scanning NMR; electron microscopy including staining of samples; infrared microprobe; secondary ion mass spectroscopy; and atomic force microscope.

An emulsion according to the present invention is produced by forming a first curable water-in-oil high internal phase emulsion by gradually adding and mixing an aqueous solution optionally containing an electrolyte into a monomer solution (oil phase) containing a mixture of polymerizable monomers and a surfactant. A polymerization initiator is added either in the monomer solution or the aqueous solution before mixing or after formation of the emulsion depending on the desired process conditions. A second such emulsion is then similarly prepared. The two emulsions are then combined in a manner that results in the desired phase separation of the cured polymer foam. The curable water-in-oil high internal phase emulsions are then cured (polymerized and crosslinked) by heating the emulsion at a temperature of at least about 25° C. for a time effective to cure the monomers. The curing is performed at a rate that results in substantial crosslinking before substantial diffusion of monomers between the emulsions occurs.

The mixture of polymerizable monomers generally contains one or more vinyl monomers and one or more crosslinking agents. Various monomers may be used in the preparation of the foams, provided the monomers can be dispersed in or form an oil phase of a water-in-oil high internal phase emulsion (oil-soluble) and have a polymerizable vinyl group. Suitable vinyl monomers include, for example, monoalkenyl arene monomers such as styrene, α-methylstyrene, chloromethylstyrene, vinylethylbenzene and vinyl toluene; acrylate or methacrylate esters such as 2-ethylhexyl acrylate, n-butyl acrylate, isobutyl acrylate, t-butyl acrylate, hexyl acrylate, n-butyl methacrylate, lauryl methacrylate, and isodecyl methacrylate; conjugated diolefins such as butadiene, isoprene, and piperylene; allenes such as allene, methyl allene and chloroallene; olefin halides such as vinyl chloride, vinyl fluoride and polyfluoro-olefins; and mixtures thereof.

Suitable crosslinking agents can be any multifunctional unsaturated monomers capable of reacting with the vinyl monomers. The crosslinking agents contain at least two functional groups. The functionality can be, for example, vinyl groups, acrylate groups and methacrylate groups. Multifunctional unsaturated crosslinking monomers include, for example, difunctional unsaturated crosslinking monomers such as divinylbenzene, diethylene glycol dimethacrylate, 1,3-butanediol dimethacrylate, and allyl methacrylate and tri-, tetra- and penta-functional unsaturated crosslinking monomers such as trimethylolpropane trimethacrylate, pentaerythritol tetramethacrylate, trimethylolpropane triacrylate, and pentaerythritol tetraacrylate, glucose pentaacrylate, glucose diethylmercaptal pentaacrylate, and sorbitan triacrylate; and poly-functional unsaturated crosslinking monomers such as polyacrylates (eg. sucrose per(meth)acrylate and cellulose (meth)acrylate). Crosslinking monomers are typically present in each emulsion in an amount of from about 2 weight percent to about 70 weight percent, preferably from about 5 weight percent to about 40 weight percent based on the total monomer mixture. Some of these crosslinking monomers can be incorporated as a non-crosslinked monomer as long as at least about 2 weight percent of the crosslinking monomers are crosslinked.

Divinylbenzene is a preferred crosslinking monomer, and is typically available as a mixture with ethyl styrene is proportions of about 55:45 by weight. These proportions can be modified so as to enrich the oil phase with one or the other component. Generally, it is advantageous to enrich the mixture with ethyl styrene which simultaneously reducing the amount of styrene in the monomer blend. The preferred ratio of divinylbenzene to ethyl styrene is from about 30:70 to 55:45, most preferably from about 35:65 to about 45:55, by weight. The inclusion of higher levels of ethylstyrene imparts greater toughness without increasing the $T_g$ of the resulting copolymer to the degree that styrene does.

Suitable polymerization initiators can be water-soluble or oil-soluble. Water-soluble initiators include, for example, persulfates such as potassium or sodium persulfate and various redox systems such as ammonium persulfate together with sodium metabisulfite. Oil soluble (monomer soluble) initiators include, for example, azo compounds such as azobisisobutyronitrile; and peroxides such as benzoyl peroxide, methyl ethyl ketone peroxide, alkylperoxycarbonates such as di-2-ethylhexyl peroxydicarbonate and di(sec-butyl)peroxydicarbonate and alkylperoxycarboxylates such as t-butyl peroxyisobutyrate, 2,5-dimethyl-2,5-bis(2,3-ethylhexanoylperoxy)hexane, and t-butyl peroctoate. The preferred water-soluble polymerization initiator is potassium persulfate and the preferred oil-soluble polymerization initiators are alkylperoxycarbonates and alkylperoxycarboxylates for fast curing time.

Most preferable alkylperoxycarbonates are branched at the 1-carbon position and most preferable alkylperoxycarboxylates are branched at the d-carbon position and/or 1-carbon position. These branched alkylperoxycarbonate peroxide can be represented by the formula:

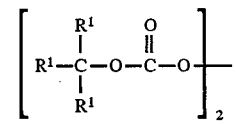

where $R^1$ is independently $C_1$ to $C_{16}$ hydrocarbons or hydrogen in which at least two of the $R^1$ are hydrocarbon groups.

The preferred branched alkyl carboxylate peroxide can be represented by the formula:

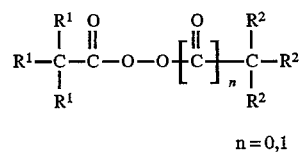

n = 0,1 where $R^1$ and $R^2$ are independently $C_1$ to $C_{16}$ hydrocarbon groups or hydrogen in which at least two of the $R^1$ or $R^2$ are hydrocarbon groups. Preferably at least two of both $R^1$ and $R^2$ are hydrocarbon groups. Hydrocarbon groups can be alkyl, alkenyl or aryl groups.

The water-soluble initiators and/or oil-soluble initiators should be present in an effective amount to cure (polymerize and to crosslink) the monomers so that the monomers are substantially polymerized and crosslinked prior to significant diffusion of monomers between the two emulsions. Typically the initiator can be present from about 0.005 to about 15 weight percent based on the monomers. The initiators can be introduced with the oil phase or the aqueous phase before or after formation of the high internal phase emulsion.

A water-soluble initiator such as potassium persulfate can be added to the aqueous solution before forming the emulsions or to the emulsions. An oil-soluble initiator can be added to the monomer solution or an advanced monomer solution or to the emulsion. Addition of a polymerization initiator to an high internal phase water-in-oil emulsion is described in U.S. Pat. No. 5,210,104, the disclosure of which is herein incorporated by reference. The initiator added to the emulsion can optionally be blended into the emulsion by any blending technique such as, for example, static mixer or a pin mixer at a low shear rate, to form a curable water-in-oil high internal phase emulsion. The rate of shear must be high enough to blend the initiator but low enough not to allow the emulsion to coalesce or liquify.

Conveniently, the initiators can be added to the oil phase (monomer phase) or aqueous phase prior to formation of the emulsion. Alternatively, at least a portion of the monomer solution can be advanced (partially polymerized) in the presence of an effective amount of an advancement initiator or by a free-radical-producing radiation source to produce an advanced monomer component prior to formation of the emulsion to reduce curing time.

To form a stable high internal phase emulsion requires that a surfactant be included in the emulsion. Such surfactant must be soluble in the oil phase used to form the emulsion. The surfactant may be nonionic, cationic, anionic or amphoteric provided the surfactant or combination of surfactants are effective to form a stable high internal phase emulsion. Preferred types of surfactants that can be used include sorbitan fatty acid esters, polyglycerol fatty acid esters, polyglycerol fatty acid esters, polyoxyethylene fatty acids and esters. In particular, sorbitan fatty acid esters such as sorbitan monolaurate ("SPAN®20"), sorbitan monooleate ("SPAN®80"), and combinations of sorbitan trioleate ("SPAN®85"), and sorbitan monooleate. One such surfactant combination is the combination of sorbitan monooleate and sorbitan trioleate in a weight ration greater than or equal to about 3:1, more preferably about 4:1. Another acceptable surfactant is "TRIODAN®20" which is a polyglycerol ester available from Grindsted and "EMSORB 252" which is a sorbitan sesquioleate available from Henkel.

Between about one and about thirty percent by weight of surfactant, based on the monomers in the oil phase, is generally sufficient, with higher oil to water ratios and higher mixing and curing temperatures generally requiring more surfactant than lower oil to water ratios and temperatures.

The type of surfactant used in making the high internal phase emulsions that are to be polymerized is important in forming water-in-oil high internal phase emulsion and the final properties of the polymerized foams obtained. The surfactants are typically added to the monomer phase (oil phase).

The amount of surfactant system must be such that a water-in-oil high internal phase emulsion will form. Generally, the surfactant system is present in an amount effective to form a water-in-oil high internal phase emulsion. Preferably, the surfactant system can be present in concentrations of from about 0.1 to about 40 weight percent, more preferably about one to about thirty weight percent based on the monomers of the particular emulsion. When saccharide fatty acid esters are used as a component of the surfactant the saccharide fatty acid surfactants are preferably present from about 0.1 weight percent to about 36 weight percent, more preferably from about 0.1 to about 25 weight percent based on the monomers. When sorbitan fatty acid esters are used as a component of the surfactant the sorbitan fatty acid ester surfactants are preferably present from about 2 weight percent to about 36 weight percent, more preferably from about 5 weight percent to about 25 weight percent based on the monomers.

The relative amounts of the aqueous phase containing water and an electrolyte and monomer phase containing monomers and surfactants used to form the high internal phase emulsions are a factor in determining the structural, mechanical and performance properties of the resulting polymeric foam phases. The ratio of water and oil in the emulsions can influence the density, cell size, and specific surface area of the foam phase. To form a polymeric foam phase with suitable density and high absorption capacity, the water-in-oil high internal phase emulsions typically contain as the internal phase, at least about 70 weight percent of water, based on the emulsion, corresponding to a water to oil weight ratio of at least about 7:3, more preferably at least about 90 weight percent of water, most preferably at least about 95 weight percent of water, corresponding to a water to oil weight ratio of at least about 20:1.

The internal aqueous phase preferably contains a water-soluble electrolyte to stabilize the emulsion and to make the foam more water wettable. Suitable electrolytes include inorganic salts (monovalent, divalent, trivalent or mixtures thereof), for example, alkali metal salts, alkaline earth metal salts and heavy metal salts such as halides, sulfates, carbonates, phosphates and mixtures thereof. Such electrolyte includes, for example, sodium chloride, sodium sulfate, potassium chloride, potassium sulfate, lithium chloride, magnesium chloride, calcium chloride, magnesium sulfate, aluminum chloride and mixtures thereof. Mono- or di-valent salts with monovalent anions such as halides are preferred.

The formation of a water-in-oil high internal phase emulsion is dependent on a number of factors such as the monomers used, water to oil ratio, type and amount of surfactant used, mixing conditions, presence and the amount of water-soluble electrolyte. It has been found that by adding a quaternary salt to a primary surfactant such as sorbitan fatty acid ester or saccharide fatty acid ester, a stable emulsion can be formed and high water to oil ratio can be achieved resulting in high fluid absorption capacity foams.

The formation of a water-in-oil emulsion is described in U.S. Pat. No. 4,522,953, and U.S. Pat. No. 5,149,720, the disclosures of which are incorporated herein by reference. In general, to form the water-in-oil emulsion, the water can be mixed in any way up to a water to oil ratio of about 4:1. An oil-in-water emulsion becomes preferred if the water was added all at once beyond a water to oil ratio of about 4:1. Typically, the water must be added gradually with a moderate rate of shear. A small capacity mixer such as a paint mixer with a shear rate of at least about 5 $s^{-1}$ preferably at least about 10 $s^{-1}$ can be used to mix the water-in-oil emulsion. A larger mixer equipped with an impeller with a shear rate of at least about 10 $s^{-1}$ or a pin gap mixer with a shear rate of at least about 50 $s^{-1}$, preferably at least about 100 $s^{-1}$ can also be used. If the shear rate is too low, the water-in-oil emulsion may revert to a oil-in-water emulsion. It is desirable to at least have a water to oil ratio of about 9:1, preferably at least about 19:1, more preferably at least about 30:1 for a high absorbency capacity foam.

A high internal phase emulsion can be prepared in batches or continuously. To form the high internal phase emulsion in batches, the emulsion is formed in a vessel or a container by gradually adding an aqueous phase to a monomer mixture and/or advanced monomer mixture under a moderate rate of shear until the desired water to oil ratio is reached.

An individual high internal phase emulsion can be prepared continuously by initially preparing a preformed emulsion of approximately the same character as the desired emulsion by the method described above, then introducing into the preformed emulsion, both the aqueous phase and/or the oil phase in such proportions so as to produce the desired emulsion. The emulsified mass is maintained in a state of continuous shear sufficient to reduce the effective viscosity of the mass near to that of the introduced phase but not above the inherent shear stability point of the desired emulsion, and then withdrawing the prepared emulsion at the desired rate.

The aqueous phase and the monomer phase for the batch process and the continuous process can be introduced in a mixing vessel by an aqueous stream or a monomer stream, respectively, through one or more inlets. The streams can be combined prior to or after entering the mixing vessel then mixed in such a way to produce the desired emulsion. The mixing vessel is any container in which the high internal phase emulsion is made regardless of the type of mixer or mixer head used.

The curable water-in-oil high internal phase emulsions can be cured in a batch process or in a continuous process. The emulsion or aqueous stream or monomer stream can be heated prior to or after the addition of the initiator.

In a batch process, the curable high internal phase emulsion is collected in a suitable container with the desired shape and cured at a temperature at least about 25° C. for a time effective to polymerize and to cure the monomers. The emulsion is preferably polymerized and cured at a temperature within the range of about 25° C. to about 90° C., as long as the emulsion is stable at the curing temperature. Alternatively, a multiple-step process as described in U.S. Pat. No. 5,189,070 issued Feb. 23, 1993, the disclosure of which is herein incorporated by reference, can also be used. In the multi-step process the emulsion is pre-cured at a temperature of less than about 65° C. until the emulsion has a Rheometrics dynamic shear modulus of greater than about 500 pascal, (lightly gelled, having a consistency like a jelly or a gelatin referred to as "gel"), then cured at a temperature of above about 70° C. for a time effective to cure the gel. The cure can be as high as about 175° C. under a pressure sufficient to prevent the aqueous phase from boiling.

The emulsions can be heated, for example, by hot water, hot air, steam, ERR, RF, microwave or ohmic heating. The emulsions should be cured until the desired properties are obtained. Typically, to obtain a cured foam, the emulsions should be cured for at least about 8 hours, at 60° C. or at least about 1 hour at 60° C. then 3 hours at a temperature of above about 70° C. Generally, the extent of reaction after curing is at least about 85% of the monomers, preferably at least about 90%, more preferably at least about 95% (i.e., less than about 5% of free monomers), most preferably at least about 99% (i.e., less than about 1% of free monomers) in order to obtain good properties.

These foams can be optionally post-cured to improve the foam properties. Post-curing of the foam can be carried out by heating the foams at a temperature of above about 75° C., preferably greater than 90° C. by steam, hot air or other heating source. Such heating may be performed initially in a heat exchanger, oven, over heated rollers or by other means.

When the temperature is near or above the boiling point of water, pressure is preferably applied to keep the water in the liquid phase. Pressure can be applied to the emulsion, if desired, at a pressure generally from above atmospheric pressure, typically within the range of about atmospheric pressure to about 1.03 MPa (150 psig). When the temperature is about 100° C., a pressure from about 7 to 70 kPa gauge (about 1 to 10 psig) is sufficient; when the temperature is about 130° C., a pressure from about 210 to 480 kPa gauge (about 30 psig to 70 psig) is preferred. The preferred pressures will be from just above the autogenous steam pressure of the solution to about twice that pressure on an absolute pressure basis, i.e., psia. For example, the emulsion can be cured under pressure by using an autoclave operating under autogenous pressure of steam generated from pure water at a given temperature, by applying nitrogen or air pressure to prevent boiling of the emulsion or by mechanical means, such as rollers, pistons, molds, or the like.

Once the curing and/or post-curing process is completed, the water incorporated in the foam may be removed or squeezed out, dried by heat or flashed by lowering the pressure to a suitable level to evaporate the remaining liquid to give the desired degree of dryness in the product foam. These drying techniques will preferably be used after the desired state of cure is developed in the foam material.

The foams of the present invention may be washed prior to, after or between drying stages (removing at least a portion of the water) to yield an absorbent block which is especially useful for the absorption of liquids. Typically, these foams are washed to reduce the electrolyte content of the foam with a solvent such as, for example, an alcohol, a low concentration electrolyte solution (lower concentration than the water phase) such as 1% calcium chloride solution or deionized water. The washed foams can be conveniently dried by squeezing the water and/or solvent out of the foams and air or heat drying.

The foams produced by the inventive process possess high absorption capacities and good uniform properties especially suitable for use as liquid absorbent articles such as wipes, diapers and catamenial products for example.

Illustrative Embodiment

The following illustrative embodiments describe the process of the invention and are provided for illustrative purposes and do not limit the present invention.

All reagents and solvents used in the following examples were technical or reagent grade and were used without further purification unless otherwise noted. Divinylbenzene was 55% pure and contained a mixture of isomers. The inhibitor, t-butyl catechol, in both styrene and divinylbenzene remained present for the reaction.

TESTING METHODS

Free Swell ("FS")/Percent Strain/Resistance to Compression Deflection ("RTCD"):

A 2"×2" (5.08×5.08 cm) square is cut from a foam slice. The thickness of the foam sample is measured while it is dry ("dry thickness") using a dead weight thickness gage (a digital linear gage model EG-225 made by Oho Sokki) exerting 50 grams force applied to a 1.60" diameter disk. This thickness is called the "caliper." The foam square is soaked in warm 88° F. (31° C.) Syn-Urine from Jayco for 17 minutes. From the 2"×2" (5.08×5.08 cm) square, a circle of 1.129" (2.868 cm) diameter is cut. This disk is re-equilibrated in the Syn-Urine for 5 minutes. The wet disk is then weighed ("initial wet weight").

The thickness of the wet sample is measured using the same load gage ("initial wet caliper"). The disk is then placed under a 0.74 psi stress where stress is the total dead weight applied to the gage divided by the cross-sectional area. The thickness of the disk is measured under this stress after 15 minutes ("wet caliper"). After 15 minutes, the specimen disk is weighed to measure the retained fluid.

The excess urine is squeezed from the disk and the remainder of the square from which it was cut. The foam is placed in boiling deionized water for 15 minutes. The foam is washed this way several times to remove inorganics. The foam is then removed, blotted dry, then placed in a vacuum oven at 60°–70° C. and dried until the foam has fully expanded. The weight of the dry disk sample is then determined in grams ("final dry weight").

The following values were calculated from the above measurements.

Free swell=initial wet weight/final dry weight

Resistance to Compression Deflection ("RTCD")=wet weight after load at 15 minutes/final dry weight $$\% \text{ Strain} = \frac{\text{initial wet caliper} - \text{wet caliper}}{\text{initial wet caliper}} \times 100$$

Vertical Wicking Rate ("VWR"):

From a foam slice, cut at 0.35 inches (0.89 cm) thickness, a 1 to 2 cm wide strip is cut, greater than 5 cm in length. The strip of foam is clamped or taped to a metal ruler, with the bottom of the foam strip flush with the 0 mark on the ruler. The ruler and foam are placed in a container of approximately 100 ml Syn-Urine from Jayco, in an incubator at 99° F. (37° C.) so the bottom of the strip (0 mark) is barely touching the surface of the Syn-Urine (less than 1 mm). The Syn-Urine is dyed with food coloring to more easily monitor its absorption and rise in the foam. A stopwatch is used to measure the time required for the liquid level to reach 5 cm vertical height in the foam sample.

EXAMPLE 1

An emulsion was prepared by adding to a reaction vessel 10 grams of a mixture of 20 parts by weight styrene, 20 parts by weight divinylbenzene, 60 parts by weight 2-ethylhexyl acrylate and 12 parts by weight of SPAN®20 (sorbitan monolaurate, an emulsifying agents from Fluka Chemical Corporation, Aldrich Chemical Company or Imperial Chemical Industries). An aqueous phase (300 ml) was then added to the reaction vessel by dropping from a funnel at a rate of about 5 ml per minute, at ambient temperature. The aqueous phase contained 10% by weight $CaCl_2$ and 0.15% by weight potassium persulfate. The mixture was stirred using a mechanical stirrer at 200 rpm.

A second emulsion was prepared by starting with 10 grams of a mixture of 80 parts by weight styrene, 20 parts by weight divinylbenzene and 12 parts by weight SPAN®20, and then adding 300 ml of an aqueous phase identical to that used in the first emulsion in the same manner as the aqueous phase was added to the first emulsion.

Two parts by volume of the first emulsion and one part by volume of the second emulsion were then mixed in a 7.5 inch, 0.31 OD static spiral mixer using a dual barrel syringe. The mixed emulsions were then cured at 60° C. for 24 hours.

COMPARATIVE EXAMPLE A

A first monomer mixture was prepared containing 20 parts by weight styrene, 20 parts by weight divinylbenzene, 60 parts by weight 2-ethylhexyl acrylate and 12 parts by weight of SPAN®20 surfactant. A second monomer mixture was prepared containing 80 parts by weight styrene, 20 parts by weight divinylebenzene and 12 parts by weight SPAN®20 surfactant. The two monomer mixtures were allowed to stand for about eighteen hours at 60° C. and then the monomer mixtures were combined and a single emulsion was formed. The emulsion was formed by adding to a reaction vessel equipped with a mechanical stirrer mixer 6.66 grams of the first monomer mixture and 3.33 grams of the second monomer mixture and then adding an aqueous phase (300 ml) to the reaction vessel by dropping from a funnel at a rate of about 5 ml per minute, at ambient temperature, while mixing with a mechanical stirrer at 200 rpm. The aqueous phase contained 10% by weight $CaCl_2$ and 0.15% by weight potassium persulfate. The emulsion was then cured for 24 hours at about 60° C.

FIG. 1 is a strain vs. time curve for example 1 (line A) and comparative example A (line B) measured under a 0.74 psi load. It can be seen from FIG. 1 that the example had a strain of about two percent after fifteen minutes whereas the comparative example was almost nine percent. Example 1 therefore is a significantly stronger foam than comparative example A. This extra strength was not achieved by sacrificing properties such as absorbency because the water to oil ratios of example 1 and comparative example A are identical, and absorbency (free swell) is generally considered to be approximately proportional to the water to oil ratio of the initial emulsion.

To demonstrate that the foam of the example was cured prior to significant diffusion between the emulsions, glass transition temperatures were determined for the foam of example 1 and comparative example A. The foam of example 1 exhibited two glass transition temperatures; one at about 23° C. and one at about 62° C. The foam of comparative example A exhibited a single glass transition temperature of about 49° C. This dual glass transition temperatures of the foam of the example demonstrates that separate phases exist in the foam of example 1 whereas the foam of comparative example A was a foam of a single phase.

EXAMPLES 2 AND 3

Two emulsions were formed as in example 1, each containing a monomer mixture of 20 parts by weight styrene, 20 parts by weight divinylbenzene, and 60 parts by weight 2-ethylhexyl acrylate, along with 12 parts by weight, based on 100 parts by weight of monomers, of "SPAN 20®". The two emulsions differed in that one emulsion was mixed with ten parts water per part monomer mixture, and the other emulsion was mixed with fifty parts water per part monomer mixture. Equal volumes of the emulsions were combined to form foams by, for example 2, layering about 1 cm layers in a tub and curing, and for example 3, stirred together until the emulsion appeared to be homogenous. The layered emulsions tended to mix and swirl together. Example 3 therefore did not cure in distinct layers, but different foam phases were visible after the foam cured.

COMPARATIVE EXAMPLE B

An emulsion was formed as in example 1, 2 and 3, with the monomer compositions of examples 2 and 3 and a 20:1 water to monomer ratio. This ratio is approximately equivalent to the ratio of monomers in the combined emulsions of examples 2 and 3.

EXAMPLES 4, 5 AND 6

Two emulsions were formed as in the previous examples, both with monomer phases of 20 parts by weight of styrene, 20 parts by weight of divinyl benzene, and 60 parts by weight of 2-ethylhexyl acrylate. The emulsions differed in that one emulsion was prepared using a 30:1 aqueous phase to monomer phase ratio, and the other foam was prepared using 50:1 aqueous phase to monomer phase ratio. Equal volumes of the emulsions were poured into a tub in about one cm layers and cured to prepare example 4. Example 5 was prepared by combining equal volumes of the emulsions in a tub, and then swirling with a large spoon. Example 6 was prepared by combining equal volumes of the emulsions in a tub, and then mixing with a paint stirrer for one minute. The mixed emulsions were each cured in a 60° C. oven for 17.25 hours.

COMPARATIVE EXAMPLE C

An emulsion was formed as in example 1–6, with the monomer compositions of examples 2–6 and a 40:1 water to monomer ratio. This ratio is equivalent to the ratio of monomers in the combined emulsions of examples 4–6.

In the TABLE below, the wicking time, resistance to compression deflection ("RTCD"), free swell, and percent strain at 15 minutes is given for examples 2–6 and comparative examples B and C.

TABLE

| EXAMPLES | WICKING TIME-SEC. | RTCD | FREE SWELL | % STRAIN |
| --- | --- | --- | --- | --- |
| 2 | 116 | 15.2 | 20.3 | 21.5 |
| 3 | 104 | 12.6 | 13.8 | 10. |
| B | 126 | 12.7 | 13.4 | 12.5 |
| 4 | 60 | 19.6 | 37.8 | 49.1 |
| 5 | 99 | 22.1 | 37.7 | 57 |
| 6 | 185 | 16.4 | 39.5 | 59.3 |
| C | 63 | 17.4 | 34.3 | 46.4 |

From the TABLE, it can be seen that compared to examples 2 and 3, comparative example B had a slow wicking time and was not significantly superior to the examples in any of the tests. Example 2, in particular, was significantly softer, as indicated by the greater percent strain, and also was able, when not under pressure, to absorb more liquid, as indicated by the greater free swell. Although the wicking time of comparative example C was good, comparative example C was not as soft as examples 4, 5, and 6, and has slightly less free swell.

Examples 2–6 and comparative examples B and C demonstrate that different combinations of properties can be achieved by combining two emulsions in different ways when compared to formation of a foam from a single emulsion of the same components.

We claim:

1. A process for the production of a porous crosslinked polymeric foam comprising the steps of:
   providing a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) at least 70 weight percent, based on the emulsion, of water as the internal phase (iii) an effective amount to produce the water-in-oil emulsion of a first surfactant, and (iv) a first polymerization initiator;
   providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) at least 70 weight percent, based on the emulsion, of water as the internal phase (iii) an effective amount to produce the water-in-oil emulsion of a second surfactant, and (iv) a second polymerization initiator;
   combining the first and second emulsions; and
   curing said polymerizable monomers under conditions effective to polymerize and crosslink the polymer prior to significant diffusion between the emulsions;
   wherein the first emulsion is an emulsion that, after curing and water removal, will be a hydrophobic foam, and the second emulsion is an emulsion that, after curing and water removal, will be a hydrophilic foam.

2. The process of claim 1 wherein the emulsions are combined by layering emulsion layers on each other.

3. The process of claim 1 wherein the emulsions are combined so that pillars of one phase of foam exist within a sheet of another phase of foam.

4. The process of claim 3 wherein the pillars are of a harder foam and the other phase of foam is a softer phase.

5. The process of claim 1 wherein the emulsions are combined by mixing the emulsions.

6. The process of claim 5 wherein the first emulsion comprises a mixture of polymerizable polymers comprising 20 parts by weight styrene, 20 parts by weight divinylbenzene, 60 parts by weight 2-ethylhexyl acrylate and the second emulsion comprises a mixture of polymerizable monomers comprising a mixture of 80 parts by weight styrene, 20 parts by weight divinylebenzene.

7. The process of claim 6 wherein the first surfactant and the second surfactant comprise sorbitan monolaurate in an amount of between about 5 and about 25 parts weight based on 100 parts by weight of polymerizable monomer in the respective emulsion.

8. A process for the production of a porous crosslinked polymeric foam comprising the steps of:
   providing a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) at least 70 weight percent, based on the emulsion, of water as the internal phase (iii) an effective amount to produce the water-in-oil emulsion of a first surfactant, and (iv) a first polymerization initiator;
   providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) at least 70 weight percent, based on the emulsion, of water as the internal phase (iii) an effective amount to produce the water-in-oil emulsion of a second surfactant, and (iv) a second polymerization initiator;
   combining the first and second emulsions; and
   curing said polymerizable monomers under conditions effective to polymerize and crosslink the polymer prior to significant diffusion between the emulsions,
   wherein the first emulsion is an emulsion that, after curing and water removal, will be a foam exhibiting a strain of greater than twenty percent after five minutes (measured under a 0.74 psi load), and the second emulsion is an emulsion that, after curing and water removal will be a foam exhibiting a strain of less than twenty percent (measured under a 0.74 psi load).

9. A process for the production of a porous crosslinked polymeric foam comprising the steps of:

provlding a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) at least 70 weight percent, based on the emulsion, of water as the internal phase (iii) an effective amount to produce the water-in-oil emulsion of a first surfactant, and (iv) a first polymerization initiator;

providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) at least 70 weight percent, based on the emulsion, of water as the internal phase (iii) an effective amount to produce the water-in-oil emulsion of a second surfactant, and (iv) a second polymerization initiator;

combining the first and second emulsions; and curing said polymerizable monomers under conditions effective to polymerize and crosslink the polymer prior to significant diffusion between the emulsions, wherein the first emulsion is an emulsion that, after curing and water removal, has a volume average pore size of greater than 50 microns, and the second emulsion is an emulsion that, after curing and water removal, has a volume average pore size of less than 50 microns.

10. A process for the production of a porous crosslinked polymeric foam comprising the steps of:

providing a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) at least 70 weight percent, based on the emulsion, of water as the internal phase (iii) an effective amount to produce the water-in-oil emulsion of a first surfactant, and (iv) a first polymerization initiator;

providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) at least 70 weight percent, based on the emulsion, of water as the internal phase (iii) an effective amount to produce the water-in-oil emulsion of a second surfactant, and (iv) a second polymerization initiator;

combining the first and second emulsions; and curing said polymerizable monomers under conditions effective to polymerize and crosslink the polymer prior to significant diffusion between the emulsions, wherein the first emulsion comprises a mixture of polymerizable polymers comprising 20 parts by weight styrene, 20 parts by weight divinylbenzene, 60 parts by weight 2-ethylhexyl acrylate and the second emulsion comprises a mixture of polymerizable monomers comprising a mixture of 80 parts by weight styrene, 20 parts by weight divinylebenzene.

11. A process for the production of a porous crosslinked polymeric foam comprising the steps of:

providing a first water-in-oil emulsion comprising (i) a first mixture of polymerizable monomers comprising at least one oil-soluble vinyl monomer and from about 2 to about 70 weight percent, based on the mixture, of a multifunctional unsaturated crosslinking monomer, (ii) water as the internal phase (iii) an effective amount to produce the water-in-oil emulsion of a first surfactant, and (iv) a first polymerization initiator;

providing a second water-in-oil emulsion comprising (i) a mixture of polymerizable monomers comprising at least one oil-soluble vinyl monomer and from about 2 to about 70 weight percent, based on the mixture, of a second multifunctional unsaturated crosslinking monomer, (ii) water as the internal phase (iii) an effective amount to produce the water-in-oil emulsion of a second surfactant, and (iv) a second polymerization initiator;

combining the first and second emulsions; and curing said polymerizable monomers under conditions effective to polymerize and crosslink the polymer prior to significant diffusion between the emulsions, wherein the first emulsion comprises water and polymerizable monomer in a ratio of between about 10:1 and about 30:1, and the second emulsion comprises water and polymerizable monomers in a ratio of about 50:1.

* * * * *